United States Patent [19]
Shell

[11] Patent Number: 5,582,837
[45] Date of Patent: Dec. 10, 1996

[54] ALKYL-SUBSTITUTED CELLULOSE-BASED SUSTAINED-RELEASE ORAL DRUG DOSAGE FORMS

[75] Inventor: John W. Shell, Hillsborough, Calif.

[73] Assignee: Depomed, Inc., Foster City, Calif.

[21] Appl. No.: 453,144

[22] Filed: May 30, 1995

Related U.S. Application Data

[63] Continuation-in-part of Ser. No. 201,490, Feb. 24, 1994, abandoned, which is a continuation of Ser. No. 986,952, Dec. 8, 1992, abandoned, which is a continuation-in-part of Ser. No. 858,320, Mar. 25, 1992, abandoned.

[51] Int. Cl.$^6$ .............................. A61K 9/16; A61K 9/22; A61K 9/52

[52] U.S. Cl. ................ 424/451; 424/452; 424/457; 424/464; 424/465; 424/468; 424/489; 514/781; 514/786; 514/951; 514/925

[58] Field of Search .................................... 424/451, 452, 424/457, 464, 465, 468, 489

[56] References Cited

U.S. PATENT DOCUMENTS 5,007,790  4/1991  Shell .......................... 424/451

Primary Examiner—James M. Spear
Attorney, Agent, or Firm—Townsend and Townsend and Crew LLP

[57] ABSTRACT

Sustained release oral drug dosage forms that comprise a tablet or capsule containing a plurality of particles of a solid-state drug dispersed in alkyl cellulose such as hydroxyethylcellulose or hydroxypropylcellulose. Once ingested the tablet or capsule disintegrates to disperse the particles into the stomach where they imbibe water to cause them to swell and also to become slippery, thus enhancing their retention in the stomach. Imbibed water from the gastric fluid dissolves the drug entrapped in the particles and the resulting solution diffuses from the dispersed particles, assuring that no solid drug, which with some drugs is more irritating, contacts the mucosal tissue. A number of embodiments of the dosage form utilizing different drugs are exemplified and the benefits are explained. Aspirin is one example.

34 Claims, 2 Drawing Sheets

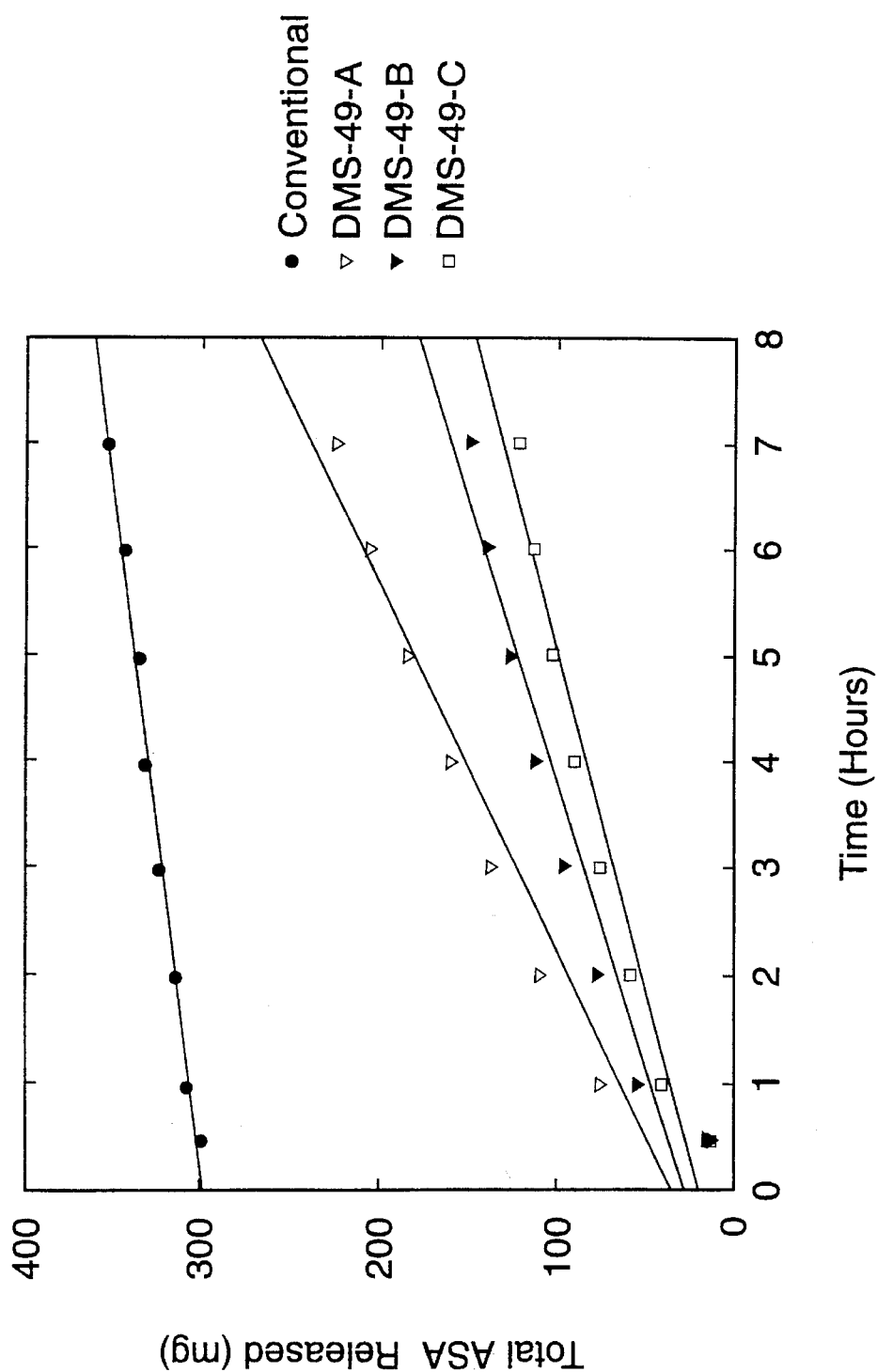

ALKYL-SUBSTITUTED CELLULOSE-BASED SUSTAINED-RELEASE ORAL DRUG DOSAGE FORMS

CROSS-REFERENCE TO RELATED APPLICATION

This application is a continuation-in-part of patent application U.S. Ser. No. 08/201,490 filed Feb. 24, 1994 now abandoned, which is a file-wrapper-continuation of patent application U.S. Ser. No. 07/986,952 filed Dec. 8, 1992 (now abandoned), which is a continuation-in-part of patent application U.S. Ser. No. 07/858,320, filed Mar. 25, 1992 (now abandoned).

TECHNICAL FIELD

This invention is in the general field of pharmacology and relates specifically to alkyl-substituted cellulose-based sustained-release drug dosage forms whose rate of drug release and dissolution is not dependent upon crosslinking and that may be made by direct compression and other procedures without binders.

BACKGROUND OF THE INVENTION

This invention is an improvement on the sustained-release oral drug dosage forms described in U.S. Pat. No. 5,007,790. Those dosage forms consist of a plurality of solid particles composed of a solid drug dispersed in a hydrophilic water-swellable crosslinked polymer. The polymers of the particle imbibe water, causing the particles to swell and the drug contained in the particle to dissolve and leach from the particle. After the drug has leached from the particles, the crosslinks of the polymer cleave to allow the polymer to dissolve.

In contrast to the polymers described in U.S. Pat. No. 5,007,790, the polymers used in the present invention are not crosslinked. They are thus inherently safer in that possible toxicity from any residual crosslinking agent is avoided. In addition, the particles made from the present polymers may be formed into solid bodies (e.g., tablets) by direct compression without binders. Binders had to be added to the polymers of the prior patent in order to compression-mold the particles. This lack of binder makes the dosage forms easier to fabricate and less expensive. Finally, once the particles have been ingested and they imbibe water, they swell to a size which promotes retention, and they become exceptionally soft and slippery. As a consequence of the latter, they tend to resist expulsion from the stomach by the peristaltic motion of the stomach walls better than the particles of the prior patent.

Hydroxyalkylcelluloses have been used commercially as binders for sustained release tablets, and as ingredients in ophthalmic preparations.

SUMMARY OF THE INVENTION

The invention is a sustained-release oral drug dosage form for releasing a solution of a drug into the stomach comprising a plurality of solid particles or pellets of a solid-state drug dispersed within a non-crosslinked alkyl-substituted cellulose that (i) swells unrestricted dimensionally via imbibition of water from gastric fluid to increase the size of the particles to promote gastric retention of the pellets in fed-mode induced patients, and makes the particles slippery to further promote their retention within the stomach, (ii) permits dissolution of the dispersed drug by imbibed gastric fluid while the drug is within the particle and release of the resulting solution, thus assuring that only drug in solution (which is less irritating than solid-state drug crystals) contacts the gastric mucosa, (iii) protects undissolved drug in the particles from stomach enzymes or pH effects so that undegraded drug is delivered to the stomach or duodenum, and (iv) maintains its physical integrity over at least a substantial portion of the time period during which the drug is released into the stomach and then dissolves, wherein the dosage form is in the form of individual particles. When presented in the form of a tablet or capsule that maintains the particles in a packed mass prior to their ingestion, the tablet or capsule rapidly disintegrates in the gastric fluid to permit the particles to disperse in the stomach.

BRIEF DESCRIPTION OF THE DRAWINGS

FIGS. 1 and 2 are graphs of the release experiments described in Example 1, infra.

DESCRIPTION OF THE PREFERRED EMBODIMENT

Figure 1:
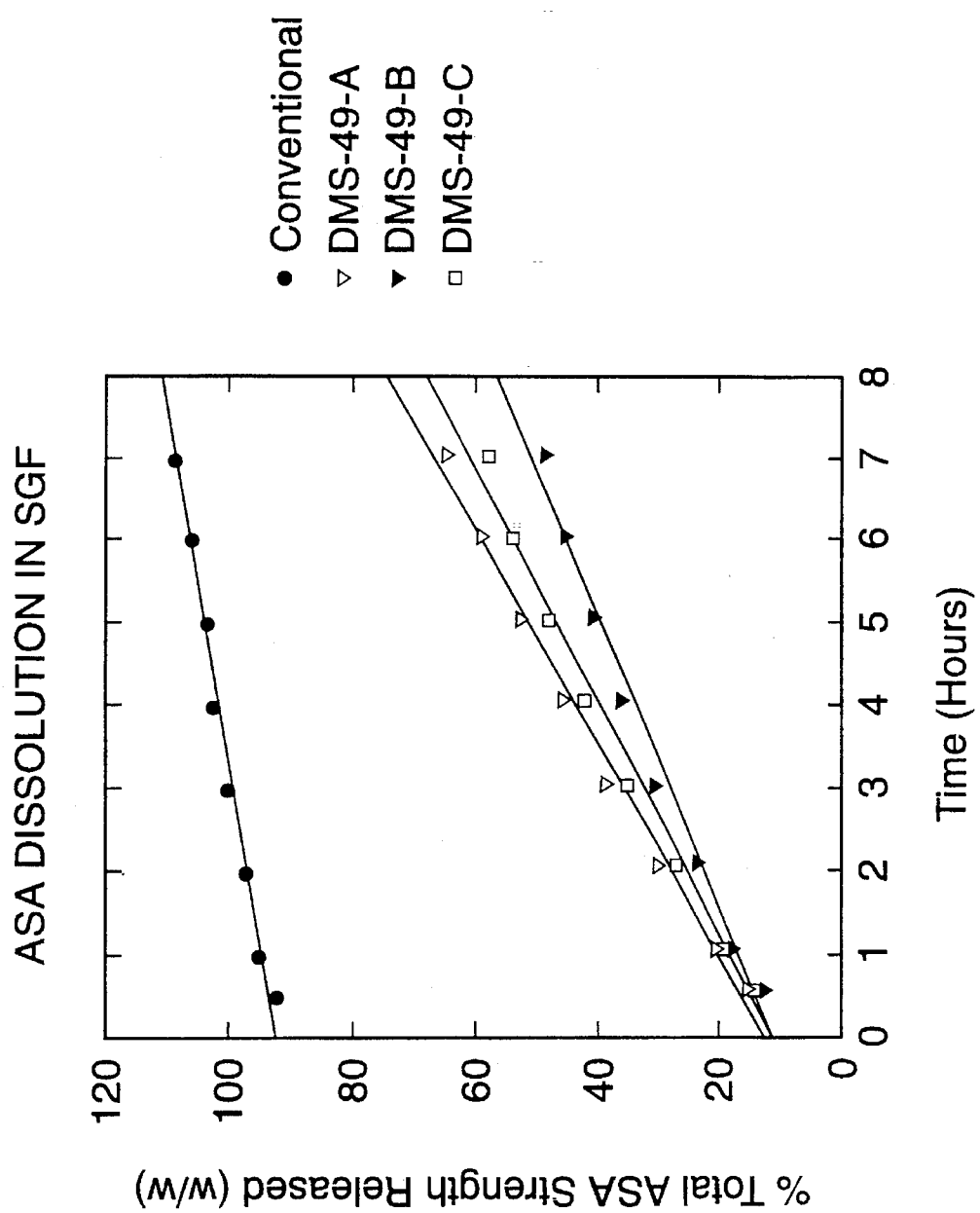

The dosage forms of the present invention are effective for administering drugs of limited solubility in gastric fluid that are capable of acting locally within the gastrointestinal tract or systemically by absorption into circulation via the gastrointestinal mucosa. The drug should be solid and not so water-soluble that it is rapidly leached from the particles over a very short time (i.e., less than about two hours), nor so insoluble that too little is leached from the particles to achieve the desired therapy. Thus, drugs having a solubility that permits them to dissolve and leach from the particles at a rate that provides the effective level for therapy and the desired duration of treatment are selected. Normally, the solubility of the drug (measured in water at 37° C.) will be in the range of 0.01% to about 35% by weight, more normally 0.01% to 5% by weight.

The invention is particularly useful for delivering drugs that, as a solid, are irritating to the gastrointestinal tract such as the mucosa of the stomach, drugs that are efficacious when administered in a sustained manner within the stomach, and drugs that under other conditions are labile in the environment of the stomach. For instance, aspirin, which may be highly injurious to the gastric mucosa in its solid state, is advantageously administered in either high doses (generally 300 to 1400 mg over 8–14 hours) for analgesia or arthritis or at low doses (usually 20 to 100 mg, preferably about 80 mg) over a 4 to 8 hour period for prevention of heart attack and stroke, reduced risk of colon or rectal cancer, prevention of migraine, or prevention of pregnancy-induced hypertension. Irritation is avoided or limited because the initially solid drug is slowly released in solution and also because the drug-containing particles are dispersed, thereby limiting the concentration of drug at any one site. The controlled delivery from the present particles allows for treatment with less total amount of drug, which further reduces the irritation effect.

Drugs which are effective for eradicating *Helicobacter pylori* from the submucosal tissue of the gastrointestinal tract, particularly the stomach, to treat stomach and duodenal ulcers, to treat gastritis and esophagitis, and reduce risk of gastric carcinoma may also be administered effectively via the invention because the invention provides enhanced gastric retention and prolonged release. Drugs and drug combinations suggested for this indication include bismuth salts such as bismuth subsalicylate and bismuth citrate, metronidazole, and amoxycillin, other antibiotics such as thiamphenicol, tetracycline, neomycin or erythromycin, or combinations of such drugs. Preferred drugs for this indication are a bismuth salt plus metronidazole, amoxycillin plus metronidazole, and amoxicillin or a bismuth salt plus omeprazole.

Alternatively, the invention can be used with conventional ulcer treating drugs such as an H-2 antagonist (e.g., cimetidine or ranitidine) or an antacid such as calcium carbonate. In this regard, some agents appear to be more effective in an acidic stomach; hence the presence of such acid reducing agents may be desirable.

Drugs such as peptides and proteins which are labile to the effects of gastric pH or gastric enzymes may also be effectively administered via the invention because the undissolved portion of the drug is physically protected within the particle until its dissolution and release, allowing for continuous delivery of undegraded drug at or near the site for the most efficient absorption of many such drugs—e.g., from the lower stomach through the duodenum to the upper part of the small intestine which is the site within the gastrointestinal tract for the most efficient absorption of many molecules which are too large for significant absorption elsewhere. The ultimate advantage of this feature is that it allows for the oral administration of some therapeutic agents which otherwise require administration by injection. Examples of such agents are calcitonin, calcitriol and insulin. Another example is that group of drugs known as proton pump inhibitors, such as omeprazole, which benefit from the slow release to optimize absorption while being protected from gastric acid.

This feature also allows for enhanced opportunity for bioabsorption of therapeutic agents which, while they may be absorbed to some extent from the G.I. tract, they are not under normal circumstances efficiently absorbed. Examples of such agents are captopril, cyclosporins, acyclovir, cephalosporins, interleukins, nitrofurantoin, and the ergot alkaloids.

Since it provides drug by continuous delivery instead of the pulse-entry associated with conventional dosage forms, two particularly significant benefits obtained with the present invention are: (1) The reduction in side effects from the drug, and (2) The ability to effect treatment with less frequent administration of the drug(s) being used. The following drugs when formulated in accordance with the invention provide these advantages, as well as other advantages as noted: Reduction in the side effects of angioedema, and agranulocytoses from angiotensin converting enzyme inhibitors such as enalapril maleate and captopril; reduction of anti-cholinergic (drying) and sedative side effects while providing long-lasting desired effects of antihistamines, such as clemastine fumarate; prolonged activity through gastric retention, less frequent administration requirements, and reduced side effects such as liver dysfunction, rhabdomyolysis, rash and headache, from cholesterol lowering drugs such as lovostatin; provision of more prolonged effects of antidepressant agents such as fluoxetine, with a reduction of typical side effects of these agents, such as insomnia and stomach upset; reduction in the required administration from three or four times daily to once daily, and reduction of the side effects, of antiepileptic drugs such as carbamazepine; and steady, prolonged control of pain, with reduced drug toxicity, from potent analgesics such as meperidine are obtained.

Benefits by way of reduction of the level of irritation may be obtained through use of formulations of this invention with blood platelet aggregation inhibitors such as ticlopidine.

A variety of similar benefits may be obtained with other types of drugs. Thus, provision, via controlled sustained delivery and gastric retention, of medication prolonged sufficiently to extend through the night so as to alleviate early morning hypertension, the cause of many heart attacks; and also reduction in the required frequency of administration to once daily dosing; of calcium channel blockers, such as verapamil, diltiazem, nifedipine, or nicardipine are obtained. Use of the invention provides, via gastric retention of the system, for more effective utilization of gastrointestinal prokinetic agents such as cisapride. The invention also enhances the treatment of gastroesophageal reflux disease by providing prolonged, local effects of agents that improve the competency of lower esophageal sphincter (LES) muscles. Such agents, which act directly on the LES muscles, include pentagastrin, PG-F2, and metaclopramide.

Other drugs that may be advantageously administered via the invention include, without limitation, H-2 antagonists or calcium carbonate for ulcer treatment/prevention; non-steroidal anti-inflammatory agents (NSAIDS) such as indomethacin, ibuprofen, naproxen and piroxicam; steroids such as prednisone, prednisolone and dexamethasone; other NSAIDS such as diclofenac and ketorolac; acyclovir for the treatment of viral diseases such as herpes; tamoxifen for treatment of cancer; chlorpheniramine maleate for allergic disorders; potassium chloride for potassium supplementation, and peptides or other labile molecules such as protease inhibitors for treating AIDS.

The solid drug or drugs are dispersed in the selected alkyl-substituted cellulose such as hydroxyethylcellulose or hydroxypropylcellulose which ultimately dissolve in the gastrointestinal (G.I.) tract in a predictably delayed manner. The hydrophilicity and water swellability of these polymers cause the drug-polymer particles to swell in size, become slippery, and in the gastric cavity permit the ingress of water into the particle. The release rate of the drug(s) from the particles is primarily dependent upon the rate at which the drug(s) is leached from the particles, which in turn is related to the dissolution rate of the drug, the particle size and drug concentration in the particle. Correlatively, because these polymers dissolve very slowly in gastric fluid, the particles maintain their integrity over at least a substantial portion (i.e., at least about 90% and preferably over 100% of the intended dosing period). Thereafter the polymer will slowly dissolve. As indicated previously, such dissolution does not involve chemical degradation (i.e., cleavage of crosslinks) of the polymer and its dissolution is thus innocuous. Typically the polymer will have completely dissolved within 8 to 10 hours after the intended dosing period.

All alkyl-substituted cellulose derivatives in which the alkyl groups have 1 to 3 carbon atoms, preferably 2 carbon atoms, and having suitable properties as noted are contemplated. Cellulose is used herein to mean a linear polymer of anhydroglucose. Additional examples of suitable alkyl-substituted cellulose are: methylcellulose, hydroxymethylcellulose and carboxymethylcellulose. In general, suitable alkyl-substituted celluloses have a mean viscosity from about 1,000 to 4,000 centipoise (1% aqueous solution at 20° C.); other suitable alkyl-substituted celluloses may fall in a viscosity range from about 100 to 6,500 centipoise (2% aqueous solution at 20° C.). A preferred polymer is hydroxyethylcellulose available from Aqualon Company (Wilmington, Del.) referred to as Natrasol® 250HX, NF. It has a viscosity of a 1 percent solution at 20° C. of from 1500 to 2500 centipoise.

The drug/polymer mixture is in the form of a plurality of particles. The solid drug is preferably dispersed homogeneously in the polymer, although it need not be. The weight ratio of drug to polymer in the mixture or dispersion will normally be 1:9 to 9:1, preferably 1:1 to 9:1, and most preferably 4:1 to 9:1. The particles are preferably spherical in shape but may be in the shape of less regular, but equant, granules.

The swollen particles will be of a size that promotes their retention in the stomach when the patient is not in the fed mode (i.e., presence of food) and particularly when the patient is in the fed mode. This will normally be in the range of about 6 to 18 mm, preferably about 6 to about 12 mm (measured as the diameter for spherical particles or largest dimension for irregularly shaped particles), but may be larger. Since the particles will typically swell up to twice their original diameter in from one to 3 hours and up to three times their original diameter in about 5 hours, the initial particle size is usually in the range of about 3 to 9 mm. Because the particles retain their physical integrity during the dosing period, their swollen volume will decrease only slowly over the dosing period.

The particles may be formed into a packed mass for ingestion by conventional techniques. For instance, the particles may be encapsulated as a "hard-filled capsule" or a "soft-elastic capsule" using known encapsulating procedures and materials. The encapsulating material should be highly soluble so that the particles are rapidly dispersed in the stomach after the capsule is ingested. Alternatively, the particles may be mixed with tableting excipients and compressed into a tablet. Each unit dose, whether capsule or tablet, will preferably contain particles of a size which when swollen enhance the potential for gastric retention. With respect to the number of particles per unit dose, a useful quantity for addition to a size zero capsule is about 7 particles, preferably spheres of about 4 mm diameter, or 25 spherical particles of about 3 mm diameter. In the preferred embodiment utilizing a tablet dosage form, the tablet contains, in addition to any inert matrix that may be utilized, from about 2–25 spherical particles of a size range from about 3 to about 9 mm in diameter.

Another additive for the inert matrix in the dosage form may be desirable when the selected drug is so soluble that it may be released at a rate more rapid than desired. Examples of such drugs are potassium chloride and various peptides used as pharmaceuticals. In order to reduce the rate of release of these high solubility drugs, the particles are formulated to include a long chain fatty acid ester of glycerin, such as glyceryl monooleate. As illustrated in the examples below, the glyceryl ester is first mixed with the selected drug and thereafter the drug/glyceryl ester combination is mixed with the cellulose polymer. In general, long chain fatty acid esters of glycerin in which the fatty acid moiety has 15 to 21 carbon atoms bonded to its carboxyl group are contemplated, with the monoester of glycerin being preferred. Both saturated and unsaturated fatty acids may be utilized in ester formation, including palmitic, stearic, oleic, linoleic and linolenic acids. In addition to glycerin monooleate, other preferred esters are glyceryl behenate and glyceryl monostearate. Suitable reduction in release rate of the drug is obtained by incorporating an effective amount of the selected glyceryl ester. In general, highly soluble drugs will exhibit the desired reduced release rate by adding about 0.5 to 4 moles of the glyceryl ester for each mole of drug.

The particulate drug/polymer mixture may be made by a number of mixing and comminution techniques with the final particle being fabricated by one of the following five methods:

(1) Extrusion and spheronization, using for example a Luwa Corporation Extruder/Marumerizer, available from Luwa Corporation Process Division, Charlotte, N.C.

(2) Direct compression, using multicavity hemispherical punches and dies, available from Elizabeth Carbide Die Company, Inc., McKeesport, Pa. The punches and dies are fitted to a suitable rotary tableting press, such as the Elizabeth-Hata single-sided Hata Auto Press machine, with either 15, 18 or 22 stations, and available from Elizabeth Hata International, Inc., North Huntington, Pa.

(3) Injection or compression molding using suitable molds fitted to a compression unit, such as available from Cincinnati Milacron, Plastics Machinery Division, Batavia, Ohio.

(4) Rotogranulation, using equipment for this procedure available from Glatt Air Techniques, Inc., Ramsey, N.J.

(5) For non-spherical shapes, the method consists of the following steps: (a)compaction of the powder mix, (b) milling of the compacted mass, (c) selective sieving of the milled product, and (d) recycling the material not selected by the sieving process.

When direct compression is used as the manufacturing process to make spheres, the addition of lubricants may be helpful and sometimes very important to prevent "capping" of the particle when the pressure is relieved. This is increasingly important as smaller spheres or particles are made. Useful agents include magnesium stearate (in a concentration in the powder mix of from 0.25% to 3%, preferably less than 1% by weight), and hydrogenated vegetable oil (about 1% to 5% by weight, preferably about 2% by weight). Hydrogenated vegetable oil is an NF (The National Formulary) substance comprising hydrogenated and refined triglycerides of stearic and palmitic acids. Additional excipients may be added to enhance powder flowability and reduce adherence in the tableting process.

Alternatively, capping may be eliminated with lower concentrations of the lubricants or other excipients if a unit shape is chosen part way between a sphere and a right cylinder. That is, the unit is a cylinder with convex, instead of flat, ends. Thus another embodiment of the invention is a plurality of pellets, instead of spheres, which are either prolate or oblate spheroids of approximately equant dimensions. That is, the diameter of the circular cross-section is near but is not equal to the length of the axis normal to the section. As with the sphere dimensions described elsewhere, this dimension is from about 3 to about 9 mm.

The dose of drugs from conventional medication forms is specified in terms of drug concentration and administration frequency. In sharp contrast, because it delivers a drug by continuous, controlled release, a dose of medication from the system described in the invention is specified by drug release rate, and by duration of the release. It is the continuous, controlled delivery feature of the system that allows for (a) reduced drug side effects, since only the level needed is provided to the patient, and (b) less frequent administration requirements.

Different drugs have different biological half-lives, which determine their required frequency of administration (once daily, four times daily, etc.). Thus, when two or more drugs are co-administered in one conventional medication unit, an unfavorable compromise is often required, resulting in an underdose of one drug and an overdose of the other. In an alternate dosage form of this invention, a plurality of drug-containing spheres are provided, some of the spheres containing a first drug/polymer composition, and designed to release its drug at its ideal rate and duration (dose), while other spheres may contain and release a second drug with the same or different polymer than used with the first drug at its ideal rate and duration which is different from the other drug. Control of the release rate of the differing drugs may also be obtained by combining different amounts of each of the drug/polymer particles in a common dosage form such as a tablet. For example, where two drugs are combined in a tablet made from 20 particles, 5 particles may contain one drug and 15 particles would contain the other drug.

Examples of drug combination products based on the invention are norethindrone plus ethinyl estradiol, a combination useful for fertility control, and acetaminophen plus codeine, a potent analgesic combination. In both examples, each single ingredient can be provided at its optimum release rate for optimum pharmacokinetics and biological activity.

This feature of the invention which allows for co-administration of physically separated drugs also allows for combination products which are otherwise impossible due to chemical incompatibility of the chosen drugs when formulated together.

EXAMPLE 1

Experimental pellets were made by mixing dry hydropropylcellulose (HPC) (Klucel, H. F., Hercules) and dry aspirin (ASA) powder in varying proportions and compressing the mixture into 3 mm diameter cylinders 3 mm high. The composition of these pellets is set forth below.

| Pellet Designations | Wt (g) | WT ASA (mg) | % HPC (Wt) |
|---|---|---|---|
| DMS-49-A | 408.9 | 347.6 | 15 |
| DMS-49-B | 435.4 | 304.8 | 30 |
| DMS-49-C | 419.8 | 209.9 | 50 |

Cumulative release experiments were performed using a Vankel VK 600 (Six-Spindle Paddle Dissolution Tester) with Rotating Basket Assembly (USP Method 1 with standard 40 mesh baskets and standard ⅜" diameter shafts) at 50 rpm and 37.0° C. The release of ASA was monitored as a function of time in simulated gastric fluid. The amount of ASA was determined using a BECKMAN DU-65 spectrophotometer at wavelengths of 247 nm and 300 nm.

The release of ASA was determined at 0.5, 1.0, 2.0, 3.0, 4.0, 5.0, 6.0 and 7.0 hour time points. The release profiles for the formulations are reported in FIGS. 1 and 2. The release profile for a conventional 325 mg aspirin tablet (no HPC) is also reported.

The results indicated that the conventional ASA tablet released more than 90% ASA within half an hour, while the invention pellets showed steady controlled release of ASA over the period of investigation (7 hours).

DMS-49-A was also evaluated in gastric irritation tests on female New Zealand white rabbits. Each rabbit was anesthetized using an intramuscular injection of xylazine and ketamine, given at 5–8 mg/kg and 35–40 mg/kg, respectively. The abdomen and the cervical area was then shaved. A surgical cutdown was performed to place a catheter into the jugular vein for maintaining anesthesia throughout the entire exposure period. The maintenance anesthesia was sodium pentobarbitol given at 13 mg/kg as needed. An endotracheal tube was then inserted to facilitate normal respiration.

In the anesthetized animal model a section of the colon, immediately proximal to the cecum, was isolated with the mesenteric vascular system intact. Two ligatures were placed approximately 15–20 cm apart around the colon section. The isolated section was then freed from the remaining intestine by cutting between the ligatures, taking care to leave the vascular and nervous systems intact. A longitudinal incision was made along the entire length of the isolated colon section and the fecal material removed. The isolated colon section is then placed onto a three-cell test chamber which forms the floor of the test cell. The test cell is continuously perfused with Lactated Ringer's solution at a rate of 2.2 ml per minute using a Model 975 Harvard pump. The test chamber is allowed to equilibrate for one hour to maintain a constant temperature of 37° C. (±2° C.). After the 1 hour equilibration period, the test material and/or positive control material ("Ten K," a commercially available potassium supplement that is highly irritating to the G.I. tract) is applied to a computer-generated, randomly selected chamber. The control chamber constituted perfusion of the Ringer's solution only. The test and positive control materials were applied in solid form. Each test cell continues to be perfused with the Ringer's solution for the entire 6 hour exposure period.

A quantity of the test material was chosen such that the total milligram amount of aspirin delivered over the 6-hour exposure period was equal to the total dose of aspirin provided by the positive control.

After 6 hours of continuous exposure, each rabbit was euthanized using an intravenous injection of sodium pentobarbitol given at approximately 100 mg/kg. The isolated section of exposed colon was removed from the intestine and evaluated for macroscopic evidence of irritation for both degree (0–4) and area (0–6.40 cm$^2$). These two values are then multiplied to calculate the Irritation Index which reflects a combination of the severity of the response and the area affected. The results are reported in the table below.

| Test Material | Source | Area | Mean Irritation Index |
|---|---|---|---|
| Lactated Ringer's | 0 | 0 | 0 |
| Aspirin | 4.00 | 4.48 | 17.93 |
| DMS-49A | 2.94 | 1.61 | 5.07 |
| Ten-K | 3.44 | 4.12 | 16.24 |

As indicated, the mean irritation index for the invention formulation was approximately one-third that of the conventional aspirin formulation and the positive control formulation.

EXAMPLE 2

Aspirin tablets of the invention are manufactured according to the following four-step procedure:

(1) A combination of 149.25 Gm aspirin dry powder, 149.25 Gm dry hydroxypropylcellulose (HPC), and 1.50 Gm dry magnesium stearate is ground to 100 mesh, and mixed in a suitable blender.

(2) The above mixture is compressed into essentially spherical pellets of 3 mm diameter, using a rotary press fitted with 3 mm hemispherical, landed punches. Except for minor lossage, this procedure will result in a total mass of 300 Gm, representing approximately 15,000 pellets, with an individual weight of 20 mg per pellet.

(3) A combination of 750 mg magnesium stearate, 54.25 Gm powdered corn starch, 80 Gm lactose and 15 Gm HPC, all previously dried, are blended together in a PK blender to assure even mixing of the ingredients, while protecting from moisture. This blend may be compressed into one-inch diameter, one-quarter inch thick tablets, using a rotary tablet press fitted with punches and dies suitable for this size, and the tablets produced by this precompression ("slugging") procedure are milled in a suitable mill, and sized by sieving to produce a fraction of irregular surfaced granules of approximately 0.5–2 mm in cross section. Granules too fine or too course are recycled through the precompression, milling and sieving process in order to reduce waste.

(4) A combination of 300 Gm of pellets produced by step (2) and 150 Gm of granules produced by step (3) are directly compressed into 1.1 cm diameter, 4.0 mm thick tablets with slightly convex faces, using a rotary press and a tablet punch with slightly convex faces and a die volume set to accept 450 mg of this mixture.

Tablets so produced disintegrate within 20 minutes in the stomach following ingestion, with the release and dispersion of ten spherical pellets, which swell to a diameter of 6 mm within 120 minutes, facilitating gastric retention. The pellets collectively release 100 mg of aspirin into the gastrointestinal tract over a period of from 4 to 8 hours. During this time the aspirin is released in the solution state rather than the solid state. Moreover, the pellets disperse within the stomach. Both dispersion and solution-state delivery operate to reduce the G.I. irritation from the delivered aspirin.

EXAMPLE 3

Aspirin capsules of the invention are prepared by the same procedure outlined in Example 2, except that:

The quantities of ingredients used in step (1) are 60 Gm aspirin dry powder, 238.5 Gm dry hydroxypropylcellulose, and 1.5 Gm dry magnesium stearate.

Step (4) of Example 2 is replaced by the following procedure: 300 Gm of pellets produced by step (2) of Example 2 are utilized as feed for a capsule filling operation in which 25 spheres of 3 mm diameter size are filled into each size zero gelatin capsule.

These capsules, following ingestion, rapidly disintegrate with the dispersion of the spheres, which release a total of 100 mg over a period of from 4 to 8 hours.

EXAMPLE 4

Example 2 is repeated except that the 149.25 Gm of drug (aspirin) is replaced by 200 Gm of bismuth subcitrate or of bismuth subsalicylate.

EXAMPLE 5

The following ingredients are dried, ground and blended together in a "twin shell" blender for 210 minutes: 111.11 Gm metronidazole, 111.11 Gm bismuth subcitrate, 1.5 Gm magnesium stearate, and 76.28 Gm hydroxyethylcellulose. This mixture is compressed into spherical pellets 3 mm in diameter, using a rotary press fitted with 3 mm hemispherical tooling. This procedure produces approximately 300 Gm of pellets, each weighing 20 mg (approximately 15,000 pellets). These pellets are filled into size zero gelatin capsules, with the result that each capsule will contain 25 pellets. Upon ingestion, such capsules disintegrate rapidly in the G.I. tract, allowing dispersal of the pellets, which then swell to facilitate gastric retention, and collectively deliver 370 mg of both metronidazole and bismuth subcitrate over a period of from 4 to 8 hours to eradicate ulcer-producing local organisms.

EXAMPLE 6

Example 5 is repeated except that the 111.11 Gm of bismuth subcitrate is replaced with a like amount of amoxycillin.

EXAMPLE 7

Example 4 is repeated except that the initial ingredients and their amounts are replaced with: 150 Gm amoxycillin, 75 Gm ranitidine, 1.50 Gm magnesium stearate, and 73.5 Gm hydroxypropylcellulose. The final dosage form thus fabricated will deliver 100 mg of amoxicillin and 50 mg of ranitidine over a time period of from 4 to 8 hours.

EXAMPLE 8

Example 7 is repeated except that ranitidine is replaced by a like amount of cimetidine.

EXAMPLE 9

Example 7 is repeated except that ranitidine is replaced by a like amount of omeprazole.

EXAMPLE 10

The procedure of Example 2 is repeated except that step (2) of the example is replaced with the following. The powder mixture from step (1) is granulated using minimal amounts of glycerine/water and processed into 3 mm diameter spheres by mechanical extrusion and spheronization. To accomplish this, the flexible mass is extruded from a Luwa Xtruda Extruder (Luwa Corporation Process Division), which produces a 3 mm diameter, continuous, cylindrical extrudate; this extrudate is then broken into cylindrical pellets of 1:1.1 length-to-diameter ratio; and these pellets are then worked into spheres of 3 mm diameter by action of a Nica spheronizer and dried.

EXAMPLE 11

Step (3) of Example 2 is repeated in which 750 mg of magnesium stearate is replaced by 600 mg of hydrogenated vegetable oil.

EXAMPLE 12

Example 2 is repeated in which the ingredients of step (1) are replaced by 149.25 Gm aspirin, 15 Gm sodium chloride, 134.25 Gm hydroxyethylcellulose, and 1.5 Gm magnesium stearate.

EXAMPLE 13

Example 12 is repeated in which 15 Gm of sodium chloride are replaced by a like amount of potassium sulfate.

EXAMPLE 14

Example 2 is repeated in which the rotary press of step (2) is fitted with concave punches and cylindrical cavities to produce either prolate or oblate spheroid shapes of resulting compressions, whose circular cross sections measure from 3 to 9 mm, and whose heights measure from 3 to 9 mm.

EXAMPLE 15

Example 2 is repeated in which the process of compression by rotary press in step (2) is replaced by the process of pellet formation by injection or compression molding, using molds fitted to a suitable compression unit (Cincinnati Malacron, Batavia, Ohio).

EXAMPLE 16

Example 2 is repeated in which the process of compression by rotary press in step (2) is replaced by the process of pellet formation by use of a rotogranulator (Glatt Air Techniques, Ramsey, N.J.).

EXAMPLE 17

Example 2 is repeated in which step (2) is replaced with the following: The mixture of step (1) is compacted by use of a roller compactor, and the compacted mass is then milled in a suitable mill to reduce the particle size of the material. This material is then sieved to selectively segregate and store all particles which fall within the size range of from 3 to 9 mm. The material above or below this size range is then recycled beginning with the compaction stage.

EXAMPLE 18

Example 2 is repeated in which hydroxypropylcellulose is replaced by hydroxypropyl methylcellulose.

EXAMPLE 19

Example 2 is repeated in which hydroxypropylcellulose is replaced by carboxymethylcellulose.

EXAMPLE 20

Example 2 is repeated in which hydroxypropylcellulose is replaced by hydroxyethylcellulose.

EXAMPLE 21

Example 2 is repeated in which the mixture of step (1) is replaced by a mixture of 150 Gm of meperidine base and 150 Gm of hydroxypropyl methylcellulose, and step (2) is replaced by the extrusion/spheronization procedure of Example 1.

EXAMPLE 22

Example 21 is repeated in which the mixture of step (1) is replaced by a mixture of 100 Gm of carbamazepine USP and 200 Gm of hydroxyethylcellulose.

The final tablets produced allow for sustained anticonvulsive effects from once or twice daily administration, compared to three or four times daily administration required by conventional tablets, and also provide for reduced intensity of this drug's side effects of cardiovascular disorder, aplastic anemia, and erythematous rash.

EXAMPLE 23

Example 21 is repeated in which the mixture of step (1) is replaced by a mixture of 40 Gm of fluoxitine base and 260 Gm of hydroxyethylcellulose.

The final tablets produced allow for sustained antidepressant effects from once daily administration, compared to twice daily administration of conventional tablets, and also provide for reduced intensity of this drug's side effects of insomnia and upset stomach.

EXAMPLE 24

Example 21 is repeated in which the mixture of step (1) is replaced by a mixture of 40 Gm of lovostatin and 260 Gm of hydroxyethylcellulose.

The final tablets produced allow for sustained cholesterol-lowering effects of this drug from once daily administration, with reduced intensity of its gastrointestinal, musculoskeletal, and CNS side effects.

EXAMPLE 25

Example 21 is repeated in which the mixture of step (1) is replaced by a mixture of 20 Gm of omeprazole and 280 Gm of hydroxyethylcellulose.

The dosage form of the invention protects the reservoir of undelivered drug from acid degradation of omeprazole, which is an acid-labile drug.

EXAMPLE 26

Example 21 is repeated in which the mixture of step (1) is replaced by a mixture of 60 Gm of diltiazem and 240 Gm of hydroxyethylcellulose and the spherical pellets of step (2) are replaced by 6 mm diameter pellets which will result in a drug delivery pattern of 8–14 hour duration.

The final tablets produced disintegrate upon ingestion, releasing the spheres contained therein, which disperse and swell in the stomach, thus facilitating gastric retention of the system. Sustained effect of this cardiovascular drug through the night from once-daily, bedtime administration is also provided. Accordingly, patients receive an increased level of protection from early morning hypertension, the cause of many heart attacks.

EXAMPLE 27

Example 26 is repeated in which the mixture of step (1) is replaced by a mixture of 40 Gm of cisapride and 260 Gm of hydroxyethylcellulose.

The final tablets produced disintegrate upon ingestion, releasing the spheres contained therein, which disperse and swell in the stomach, thus facilitating gastric retention and sustained local effect of the drug. Sustained, local delivery of this prokinetic agent allows for more efficient treatment of esophageal reflux disease.

EXAMPLE 28

Example 21 is repeated in which the mixture of step (1) is replaced by a mixture of 500 mg calcitonin, 280 Gm of hydroxyethylcellulose, and 41.33 mg of glyceryl monooleate. In preparing the formulation, the calcitonin and the glyceryl monooleate are first mixed intimately, and this mixture is then added to and mixed with the hydroxyethylcellulose.

The final tablets produced disintegrate upon ingestion, releasing the spheres contained therein, which disperse and swell in the stomach, thus facilitating gastric retention of the system. Controlled delivery of this soluble drug is facilitated by the presence of glyceryl monooleate.

The delivery system of the invention protects calcitonin, a labile agent, from degradation effects of gastric acid and gastric enzymes while the system is retained in the stomach. Moreover, delivery of the agent is continuously provided from the system retained in the lower part of the stomach, through the duodenum, to the upper part of the small intestine, which is the most efficient site of absorption of molecules too large to be appreciably absorbed elsewhere. When delivered by this system, a sufficient amount of calcitonin, a large peptide hormone, is absorbed to be clinically useful from oral administration. Otherwise, this agent must be administered by injection.

EXAMPLE 29

Example 21 is repeated in which the mixture of step (1) is replaced by a mixture of 100 Gm of cyclosporin USP, an immunosuppressive agent, and 200 Gm of hydroxyethylcellulose.

The final tablets produced disintegrate upon ingestion, releasing the spheres contained therein, which disperse and swell in the stomach, thus facilitating gastric retention and, through extended time of tissue exposure, increasing the amount of absorption of this otherwise difficult-to-absorb drug. Further, by providing cyclosporin through low level, continuous delivery, the adverse effects of hepatotoxicity, nephrotoxicity, and hypertension are reduced.

EXAMPLE 30

Sustained release antacid tablets of the invention utilizing calcium carbonate as the active ingredient are prepared as follows:

(1) A combination of 197.4 Gm of dry calcium carbonate, 82.6 Gm of hydroxyethylcellulose, and 2 Gm of magnesium stearate are ground to 100 mesh and mixed in a suitable blender.

(2) The mixture from step (1) is compressed into essentially spherical pellets of 4 mm diameter, using a rotary tablet press fitted with hemispherical-cavity, landed punches and dies. Except for minor losses, this procedure will produce about 282 Gm of total pellet mass, representing about 9400 pellets, each weighing about 30 mg.

(3) The pellets of step (2) are used as a feed for a gelatin capsule filling operation in which 7 pellets are filled into each size zero capsule.

These capsules, following oral administration, rapidly disintegrate with dispersion of the pellets, which rapidly swell to promote their retention in the gastric cavity, and collectively release therein a total of 147 mg of calcium carbonate over a 6 to 8 hour time period. This sustained release of the antacid agent into the stomach allows for patients who suffer from nocturnal gastric hyperacidity and/or esophageal reflux disease to sleep through the night from a single bedtime medication of a locally active agent (i.e., no systemic side effects). Less attractive alternatives for such patients are either multiple administrations of a conventional medication during the night, a regimen which interrupts sleep, or the use of longer-acting agents for gastric acid reduction such as cimetidine or ranitidine, which act systemically and therefore have adverse side effects.

What is claimed is:

1. A sustained release oral drug dosage form for releasing a solution of a drug into the stomach comprising a plurality of solid particles of initially about 3–9 mm in diameter in maximum dimension, each particle containing a solid-state drug dispersed within a non-chemically crosslinked alkyl-substituted cellulose selected from the group consisting of hydroxyethylcellulose, hydroxypropylcellulose, hydroxypropylmethylcellulose, carboxymethylcellulose, and hydroxymethylcellulose, in a weight ratio of drug to polymer of about 1:9 to 9:1, the particles (i) swelling unrestrained dimensionally up to about three times their original diameter via imbibition of water from gastric fluid to increase the size of the particles to promote retention within the stomach, and make the particles slippery, which also promotes their retention within the stomach, (ii) permitting dissolution of the dispersed drug by imbibed gastric water while the drug is within the particle and release of the resulting solution, thus assuring that only drug in solution contacts the gastric mucosa, (iii) protecting undissolved drug from stomach enzymes or pH and duodenum, and (iv) maintaining their physical integrity over at least a substantial portion of the time period during which the drug is released into the stomach and then dissolves; and wherein the dosage form is in the form of a tablet or capsule that maintains the particles in a packed mass prior to their ingestion and then rapidly disintegrates in the gastric fluid to permit the particles to disperse in the stomach.

2. The dosage form in accordance with claim 1 wherein the cellulose is hydroxyethylcellulose.

3. The dosage form in accordance with claim 1 wherein the drug is aspirin, the sustained drug delivery time period is about 8–14 hours and the total dose of aspirin delivered is 300 to 1400 mg.

4. The dosage form in accordance with claim 1 wherein the drug is aspirin, the sustained time period is 4 to 8 hours and the dose of aspirin is 20 to 100 mg.

5. The dosage form in accordance with claim 1 wherein the drug is a *Helicobacter pylori* eradicant.

6. The dosage form in accordance with claim 5 wherein the eradicant is a bismuth salt, metronidazole, amoxicillin, or a combination thereof.

7. The dosage form in accordance with claim 5 wherein the eradicant is amoxicillin or a bismuth salt plus omeprazole, an H-2 antagonist, or an antacid.

8. The dosage form in accordance with claim 1 wherein the weight ratio of drug to polymer is about 1:1 to 9:1.

9. The dosage form in accordance with claim 1 wherein the dosage form is a tablet, the particles are spherical and about 3–9 mm in diameter, and number about 2–25 in one tablet.

10. The dosage form in accordance with claim 1 wherein the dosage form is a capsule, the particles are spherical and about 3–6 mm in diameter, and number about 3–25 in one capsule.

11. The dosage form in accordance with claim 1 wherein the particles in said tablet or capsule contain a first drug and wherein said tablet or capsule also includes particles containing a second drug which differs from said first drug dispersed within a non-crosslinked alkyl-substituted cellulose.

12. The dosage form in accordance with claim 11 wherein the number of said first drug particles differs from the number of said second drug particles, said numbers of particles being selected to provide the desired delivered dose of each of said first and second drugs.

13. The dosage form in accordance with claim 11 wherein said first drug particles contain a first cellulose polymer and said second drug particles contain a second cellulose polymer different from said first cellulose polymer, said polymers being selected to provide the desired release rates of said first and second drugs.

14. The dosage form in accordance with claim 1 wherein said drug has a release rate greater than desired because of its water solubility and including long chain fatty acid ester of glycerin in which the fatty acid moiety has 15 to 21 carbon atoms bonded to its carboxyl group, to reduce the release rate of drug to a lower rate.

15. The dosage form in accordance with claim 14 wherein the drug is potassium chloride.

16. The dosage form in accordance with claim 14 wherein the drug is a peptide.

17. The dosage form in accordance with claim 14 wherein the glyceryl ester is selected from glyceryl monooleate, glyceryl behenate and glyceryl monostearate, the selected ester/drug ratio being about 0.5 to 4 moles of ester per mole of drug.

18. The dosage form in accordance with claim 1 wherein said drug is cisapride.

19. The dosage form in accordance with claim 1 wherein said drug is calcium carbonate.

20. The dosage form in accordance with claim 1 wherein said drug is bismuth subsalicylate.

21. The dosage form in accordance with claim 1 wherein said drug is Naproxen.

22. A method for delivering an acid-labile drug through the gastrointestinal tract comprising providing a dosage form in accordance with claim 1 wherein the unprotected solid state drug is sufficiently enzyme- or acid-labile in the gastrointestinal tract as to require administration by injection, and introducing said dosage form to a human patient orally.

23. A method for reducing side effects of a drug and frequency of administration comprising providing a dosage form in accordance with claim 1, and introducing said dosage form to a human patient orally.

24. A method for reducing side effects of a drug and frequency of administration comprising providing a dosage form in accordance with claim 9, and introducing said dosage form to a human patient orally.

25. A method for reducing side effects of a drug and frequency of administration comprising providing a dosage form in accordance with claim 10, and introducing said dosage form to a human patient orally.

26. A method for reducing side effects of a drug and frequency of administration comprising providing a dosage form in accordance with claim 11, and introducing said dosage form to a human patient orally.

27. A method for reducing side effects of a drug and frequency of administration comprising providing a dosage form in accordance with claim 12, and introducing said dosage form to a human patient orally.

28. A method for reducing side effects of a drug and frequency of administration comprising providing a dosage form in accordance with claim 13, and introducing said dosage form to a human patient orally.

29. A method for reducing side effects of a drug and frequency of administration comprising providing a dosage form in accordance with claim 14, and introducing said dosage form to a human patient orally.

30. A method for reducing side effects of a drug and frequency of administration comprising providing a dosage form in accordance with claim 17, and introducing said dosage form to a human patient orally.

31. The dosage form in accordance with claim 1 wherein the cellulose is hydroxypropylcellulose.

32. The dosage form in accordance with claim 1 wherein the cellulose is hydroxypropylmethylcellulose.

33. The dosage form in accordance with claim 1 wherein the cellulose is carboxymethylcellulose.

34. The dosage form in accordance with claim 1 wherein the cellulose is hydroxymethylcellulose.

* * * * *